United States Patent [19]

Smith

[11] Patent Number: 5,073,555

[45] Date of Patent: Dec. 17, 1991

[54] MEDICAMENTS INTENDED FOR COMBINED USE IN THE IMPROVEMENT OF LYMPHOCYTE FUNCTION TO LOWER CHOLESTEROL LEVELS

[75] Inventor: R. Arnold Smith, Jackson, Miss.

[73] Assignee: George D. McAdory, Jackson, Miss.

[21] Appl. No.: 528,885

[22] Filed: May 25, 1990

Related U.S. Application Data

[63] Continuation-in-part of Ser. No. 177,121, Apr. 4, 1988, Pat. No. 4,929,640.

[51] Int. Cl.$^5$ .................... A61K 31/34; A61K 31/50; A61K 31/495

[52] U.S. Cl. ..................................... 514/252; 514/474

[58] Field of Search ................................ 514/474, 252

Primary Examiner—Stanley J. Friedman
Attorney, Agent, or Firm—Epstein, Edell & Retzer

[57] ABSTRACT

A new composition, useful as a medicament, contains ascorbate, preferably as metallic salt(s), in combination with a dopamine agonist such as bromocriptine, with the ratio by weight of ascorbate to bromocriptine being 400:1 or greater. This combination, believed to act through stimulation of pituitary production of somatotropin, has a significant ability to stimulate enhanced lymphocyte function to result in method to reduce cholesterol levels in humans.

9 Claims, No Drawings

MEDICAMENTS INTENDED FOR COMBINED USE IN THE IMPROVEMENT OF LYMPHOCYTE FUNCTION TO LOWER CHOLESTEROL LEVELS

RELATED APPLICATIONS

The present invention is a continuation-in-part of Ser. No. 07/177,121, filed Apr. 4, 1988, now U.S. Pat. No. 4,929,640.

BACKGROUND OF THE INVENTION

Phenotypic subpopulations of lymphocytes in the peripheral blood, as defined by immunofluorescent cell sorting, are believed to reflect a useful measure of a person's immune function. For conceptual purposes the lymphocytes believed to arise from the embryonic thymus can be divided into a regulatory group and an effector group. The regulatory group is typified by the OKT-3, OKT-11, OKT-4 and OKT-8 monoconal antibodies to human leucocytes marketed through the Colter Company. A clinically significant problem without ready solution is represented by a tendency of these phenotypes to fall below normal limits in several types of disease including autoimmune illness and neoplasia. The present invention, suspected to act through the hypophysis (pituitary gland) by the stimulation of somatotropin, has been found to significantly increase the OKT phenotypes designated above and, in the course of this enhancing effect, to successfully relieve or improve many autoimmune illnesses.

That the life cycle decline of somatotropin may be a fundamental cause of many medical ailments is suggested by the wide range of somatic complaints which respond to this combination. Included in these complaints are connective tissue inflammations such as arthritis, tendonitis, bursitis, and myositis. Migraine headaches, tension headaches or sinus headaches often respond. Inflammatory condition involving adenomatous viscera, including breast, lung, urinary, bladder and bowel often respond. Psychological depression typically accompanying many of these conditions is improved.

DESCRIPTION OF THE INVENTION

The present invention is a medicament that takes advantage of my discovery of a synergistic effect resulting from the combination of vitamin C (ascorbate) and a dopamine agonist having the capacity to stimulate regulatory lymphocyte populations, such as a dopaminergic ergot alkaloid, (bromocriptine, lergotrile) or pergolide. Dosage includes one or more grams of ascorbate daily, preferably as an alkalizing salt such as sodium ascorbate which has shown particular efficacy. Bromocriptine is typically used in a quantity ranging from 0.615 milligrams to five milligrams daily, the ratio by weight of ascorbate to bromocriptine being approximately 400:1 or greater. The combination produces a desired clinical effect only with a delay, and the onset of benefit usually occurs not sooner than ten days and it may take as long as a month before energy improves and the first signs of symptomatic improvement occur. By two months the beneficial effects of treatment are usually well established. The clinical pattern suggests a rate limited induction process, with a threshold of subjective response being reached after a variable delay.

Evidences that support an additive and quite possibly synergistic effect of these two agents at the hypophysis include documentation of intense concentration of ascorbate in the hypophysis by some sort of physiologic "pump" mechanism, and by evidence that bromocriptine can raise blood levels of somatotropin normal individuals. It is also documented that identical twins, when one of them receives ascorbate, show a higher growth rate in the ascorbate receiving twin, strongly suggesting somatotropin (also known as growth hormone) stimulation. Somatotropin is a polypeptide hormone currently available for pharmacological use only at great cost and is made either from human pituitary gland fractionation or through recombinant cell culture technology. Exogenous somatotropin is digested in the stomach and does not cross mucosal surfaces well, thus requiring inconvenient intramuscular or intravenous injection. Thus exogenous replacement is both expensive and, like insulin, clinically demanding in its delivery. The composition of the present invention, by stimulating endogenous production, is a much more satisfactory method for treatment of somatotropin deficiency.

The ascorbate-dopamine agonist combination may be used alone or in combination with pharmacological doses of vitamin E, as an initial induction of regulatory function. After one month of initial induction, further additions can be usefully added. To understand this sequencing one must consider the basic lymphocyte subsets in the regulatory group of OKT surface antibodies mentioned above. Two regulatory lymphocyte subsets that are often depressed in autoimmune disease are the OKT-11 and OKT-8 phenotypes. The suppressor T (thymus gland) lymphocyte (OKT-8) population suppresses effector attack on autoantigens, thus protecting the individual's own vital tissues. Healthful levels of somatotropin secretion depend on tonic stimulation of cells in the adenohypophysis by dopamine of central nervous system origin, and the thymus in turn produces hormones depending on tonic stimulation by somatotropin. Suppressor T-lymphocytes are held in tonic adequacy in turn by thymic hormone secretion. The well documented life cycle decline in thymic hormone is distinctly peripheral to the level of action of this invention, but is a component of the deficiency sequence restored or rejuvenated by the present invention. The novel medicament of the present invention acts early in this physiologic sequence at the level of dopaminergic input to the hypophysis.

Without the suppressor cell component of regulatory function at adequate levels, auto-immune illness often develops. Attempts at stimulating the effector (i.e., natural killer) component of the lymphocyte population (Leu 11 or Leu 7) usually results in increased attack on auto-antigens with flare-ups of auto-immune related illnesses and an increase in malaise. The helper inducer population OKT-4 acts as a spotter mechanism to focus immune effectors on the enemy antigen, and the immune system is unable to achieve specificity with helper inducer T-cell inadequacy. On the other hand, once the helper inducer lymphocyte population (OKT-4) and suppressor cytotoxic T-lymphocyte suppressor/cytotoxic lymphocyte subsets are restored in accordance with the present invention, then one can begin effective stimulation of the effector lymphocyte subsets with confidence that the patient's condition will not be significantly worsened but that invaders, such as viral illnesses or neoplasia, will be more effectively opposed. The effector group of lymphocytes is typified by the Leu 11 phenotypic marker (Becton Dickinson) and is believed to be significantly under leutinizing hormone control. Since leutinizing hormone effect on lymphocyte phenotype counts is mediated through the production of progestins or androgens, these agents are used in combinations of medicaments once regulatory functions have been reconstituted. The unique compositions of the present invention result in the restoration of regulatory functions that allow high doses of progestins or androgens to be used with greatly reduced autoimmune side effects.

Pharmacological studies employing (1) clinical response and (2) objective assessment by immunofluorescent lymphocyte phenotyping have proven unequivocally that the composition of the present invention is efficacious and that the effects obtained seem significantly better than clinical benefits obtained by many other types of medications that attempt to attack disease processes more peripherally in their pathophysiologic mechanism of causation. Complete blood count ("CBC") determinations can be used to monitor the percentage of lymphocytes in peripheral blood, or to calculate the absolute lymphocyte count (percent lymphocytes $\times 0.1 \times$ white blood count). This conventional test has little, if any, value in monitoring efficacy of the composition of the present invention, and the importance of immunofluorescent phenotyping for objective assessment must again be stressed.

Suitable dopamine agonists for us in the instant invention to effect lowering of cholesterol levels are dopaminergic ergot alkaloids such as bromocriptine, lergotrile or pergolide or pharmaceutically acceptable salts thereof or combinations thereof. The preferred dopamine agonist for use in the present invention is bromocriptine or pharmaceutically acceptable salts thereof such as bromocriptine mesylate.

The dopamine agonists are administered to humans in the above active compounds, preferably bromocriptine, in therapeutically effective sufficient to stimulate regulatory lymphocyte populations, namely, amounts ranging from approximately 0.4 to 10.0 milligrams daily, preferably from 0.6 to 5.0 milligrams daily.

The ascorbate source is administered conjointly with the dopamine agonists of the present invention administered in the form of ascorbic acid, sodium ascorbate, or other equivalent salt forms in somatotropin producing therapeutically effective amounts typically ranging from 0.25 grams to 20 grams on a daily basis. It has been determined that the ratio of weight of ascorbate to bromocriptine during administration of 400:1 or greater is preferred.

A preferred composition of the present invention additionally includes 0.1 to 0.3 mg of thyroxin or equivalent, physiologic mixtures of thyroxine and liothyronine and/or 0.1 to 800 milligrams of gonadal hormones are often employed to further improve both regulatory and effector lymphocyte function.

The pharmaceutical compositions of the present invention may be coadministered in a single blended formulation or the individual components may be sequentially administered. The drugs of the instant invention are preferably orally administered, in the form of troches, tablets, capsules and the like, however, other modes of administration are considered to be within the scope of the present invention.

The medicament combination of the present invention produces a delayed desired clinical effect with the onset of benefit usually occurring not sooner than ten days, and at times as long as two months before energy improves in the patient and the first signs of symptomatic improvement occur. After two months the beneficial effects of treatment are usually well established. The clinical pattern suggests a rate limited induction process, with a threshold of subjective response being reached after a variable delay.

The quantities of vitamin C and bromocriptine or other equivalent dopamine agonist described herein have been well documented as safe and acceptable for long term use when used independently of one another. Use of a combination in the quantities and ratio employed in the present invention has not been described in the prior art. While the combination of a metallic ascorbate salt and a dopamine agonist (e.g., sodium ascorbate and bromocriptine) seems to be quintessential to the effects described herein, the addition of dl-alpha-tocopherol (vitamin E) in the quantity of 400 international units, three times daily, appears to provide a moderate improvement in the patient's response rate. For patients with severe allergies, riboflavin (vitamin B2), 100 milligrams once or twice daily, was also employed.

Gonadal hormones can be administered in accordance with the methods of the present invention conjointly or sequentially with the dopamine agonist and the ascorbate, in therapeutically effective amounts ranging from 0.1 to 800 milligrams on a daily basis. Such therapeutically effective amounts vary for each type of gonadal hormone and the following amounts represent preferred therapeutic amounts for the preferred gonadal hormones.

| GONADAL HORMONE | MILLIGRAMS |
| --- | --- |
| Equine conjugated estrogen | 0.1 to 6.0 mg |
| Medroxyprogesterone acetate | 1.0 to 60 mg |
| Piperazine estrone sulfate (Estropipate) | 0.1 to 5 mg |
| Natural progesterone | 5.0 to 800 mg |
| Methyltestosterone | 1.0 to 20 mg |
| Estrone | 1.0 to 10 mg |

The following examples set out details of composition formulas suitable for use in the present invention, it being understood that further preparations suitable for the present invention may also be employed.

EXAMPLE 1

Tablets according to the formula: sodium ascorbate, 500 mg; bromocriptine, 0.21 mg; dl-alpha-tocopherol, 100 international units; riboflavin, 9 mg.

EXAMPLE 2

Tablets according to the formula: sodium ascorbate, 500 mg; bromocriptine, 0.1 mg; dl-alpha-tocopherol, 50 units; riboflavin, 4 mg.

EXAMPLE 3

Tablets according to the formula sodium ascorbate, 1 gm; bromocriptine, 0.1 mg; dl-alpha-tocopherol, 60 international units; riboflavin, 5 mg.

EXAMPLE 4

Any of above but without riboflavin.

The above examples are typical of compositions employed during the induction phase, and starting dose would typically be two tablets, three times daily, increasing up to as many as twenty-four tablets daily in three to four divided doses. The examples which follow are compositions employed once the rate-limited induction of regulatory function in the somatotropin dependent lymphocyte phenotypes has been established.

EXAMPLE 5

Sodium ascorbate, 500 mg; bromocriptine, 0.21 mg; dl-alpha-tocopherol, 100 international units; megestrol acetate, 14 mg.

EXAMPLE 6

Sodium ascorbate, 500 mg; bromocriptine, 0.21 mg; dl-alpha-tocopherol, 100 international units; equine conjugated estrogens, 0.11 mg; norethindrone acetate, 0.5 mg.

EXAMPLE 7

Sodium ascorbate, 500 mg; bromocriptine, 0.21 mg; dl-alpha-tocopherol, 100 international units; megestrol acetate, 14 mg; germanium sesquioxide, 25 mg.

Although the above examples employ the dopaminergic ergot alkaloid known as bromocriptine (i.e., 2-bromo-alpha-ergocryptine), sold commercially as Parladel, it is believed that other dopamine agonists, having the capacity to stimulate regulatory lymphocyte populations, are appropriate substitutes; lergotrile and pergolide, are examples of such dopamine agonists.

From the above examples it is clear that the bromocriptine or equivalent dopamine agonist is employed in a proportion of 1 part to 400–20,000 parts ascorbate as its salt.

The present invention produces numerous advantageous results. For example, it provides a clinically reliable method for stimulating growth hormone production in the intact hypophysis. The pharmaceutical composition is also useful in stimulating regulatory lymphocyte subsets likely dependent on somatotropin stimulation of the thymus gland.

In addition, the composition produces improvement of both regulatory and effector lymphocyte function with dl-alpha-tocopherol (vitamin E) or riboflavin often employed during induction, and with hormones of the gonadal group (progestins or androgens or estrogen) often used during the effector stimulating phase of immune enhancement which can be carried out subsequent to regulatory function enhancement. Germanium sesquioxide, a potent stimulant of Leu 11 lymphocytes, may also be added during the effector stimulant phase to more specific benefit. In other words, the dopaminergic agonist and the ascorbate, when combined with gonadal hormones and germanium sesquioxide, can, by virtue of the enhancement of regulatory function, produce a more focused attack of natural killer lymphocyte immunity effectors against invaders disruptive to the internal homeostasis.

The composition of the present invention is also believed to be effective to: relieve or improve inflammatory mesenchymal disorders such as arthritis, tendonitis, bursitis, and myositis; relieve auto-immune mediated inflammatory glandular disorders such as pancreatitis, interstitial cystitis, ulcerative colitis, and immune pneumonitis; relieve or improve auto-immune epidermal disorders such as alopecia areata or scleroderma; enhance general immune resistance to chronic viral infections such as those mediated by the herpes viridae group (Type 1 Herpes, Type 2 Herpes, Epstein-Barr Viruses, cytomegalo-virus); improve the results of progestin or androgen mediated enhancement of natural killer T-cell function by first improving the regulatory function typified by the OKT-4 group of helper-induced lymphocytes which focuses effector activity correctly against desired targets and by stimulating suppressor/cytotoxic OKT-8 T-lymphocyte population which prevent misdirected attacks of effector cells on autoantigens resulting in autoimmunity; prevent recurrent migraine headaches; and improve the loss of physical strength, loss of energy, and psychological depression which accompany disturbances of somatotropin secretion.

Treatment by the novel pharmaceutical composition of the present invention, by enhancing suppressor T-cell function, decreases the sensitivity of auto-antigens to allergic attacks instituted by various environmental allergens. For this reason the present invention is useful in treating patients suffering from severe allergic disease. Moreover, many hypochondriacs prove to have organic disease, as documented by quantifiable regulatory subset determinations below the normal range. These patients, too, will often improve when treated in accordance with the present invention.

The composition of the present invention also appears to stimulate growth of preadolescent youth.

Because of the relationship of dopaminergic exhaustion to prominent types of drug addiction (cocaine, heroine, crack), and because the composition of the present invention supports restoration of an extremely important part of dopaminergic function (i.e., growth hormone secretion), the composition appears to serve a useful role in the treatment of some common forms of drug abuse. Moreover, a principle intuitive incentive to cigarette and other tobacco addiction is the pharmacological benefit obtained by somatotropin secretagogue equivalency in tobacco. The principle problem with tobacco smoke is that it contains a plethora of highly reactive pyrochemical species that denature normal physiologic molecules, such as those of mesenchymal support, causing aging and, in chromosomes, greatly increasing gene mutation rate. A person who is a long term cigarette user faces the choice of either continuing this dangerous habit or of terminating smoking. Smoking termination, by allowing a drop in somatotropin-induced regulatory lymphocyte function, may actually encourage certain latent cancers in various stages of initiation or promotion to grow uncontrollably. Somatotropin loss also causes physiological depression, irritability, increased body fat with weight gain, and a loss in muscle mass with decrease in strength and energy. The pharmaceutical composition of the present invention, by replacing the active principle of tobacco smoke in a vastly more healthful manner, may contribute greatly to efforts to prevent or decrease tobacco use. The antioxidant properties of ascorbate stand in marked contrast to the pro-oxidant properties of pyrochemicals like those in tobacco smoke.

Even though local recurrence of radically resected cancer of breast or rectum is an initial manifestation of failure that may be a fatal development, and even though regional radiotherapy often decreases the frequency of regional relapse, the long-term survival of adjuvantly irradiated patients with these conditions is no significantly improved in most studies. The major mechanism of this failure to improve survival rate is the decimation of committed lymphocytes in the irradiated volume and the defective immunity consequent to radiotherapy. Immune depression after radiotherapy is documented in the literature. By stimulating enhanced lymphocyte function, the composition of the present invention has a role in reconstituting immunity in these patients and in other post-radiotherapy immuno depressed subjects.

It is also believed that the composition of the present invention tends to retard the destructive components of the aging process to a substantial degree. The antioxidant properties of ascorbate, in and of itself, may be useful to some extent in enhancing a sense of well-being; however, when combined with bromocriptine or equivalent dopamine agonist, the stimulatory effect on somatotropin production obtained produces a far more effective medicament. This medicament would, therefore, justify general use for those individuals who wish to retard the aging process and who find relief of disease objectively and subjectively manifest during the first two months of a therapeutic trial.

It has also been determined that the novel pharmaceutical compositions of the present invention as a benefit of stimulated enhanced lymphocyte function are useful in treating patients having high cholesterol levels. The following examples display the utility of the instant composition in lowering cholesterol levels.

EXAMPLE 8

A female patient complaining of generalized rheumatic aches and chronic fatigue and having a cholesterol level of 223 mg/dl was placed on a daily dosage regimen of: 2.5 mg. of bromocriptine; 400 international units of tocopherol three times a day; and 1 gram, three times a day of time released Vitamin C (ascorbic acid). After approximately three months of daily medication, the patient's cholesterol level was 175 mg/dl. The patient also displayed an increased energy level and substantially lessened complaints of rheumatic aches.

EXAMPLE 9

A male patient receiving post-operative pelvic radiotherapy having a cholesterol level of 212 mg/dl was placed on a daily dosage regimen of: alpha-tocophenol 400 international units three times a day; 1 gram of sodium ascorbate three times a day, 1 tablespoon (2.5 grams) of Vitamin C in aqueous solution four times a day; 300 mg. of cimetidine four times a day; one-half of a troche twice a day; containing: 2.5 mg. of bromocriptine; 30 mg. of medroxyprogesterone, 60 mg. of coenzyme Q-10; and 90 micrograms of levothyroxine sodium and 22.5 micrograms of liothyronine sodium (Euthroid). After three months of daily medication, the patient's cholesterol level was reduced to 139 mg/dl.

Having described preferred embodiments of a new medicament intended for combined use in the improvement of lymphocyte function, it is believed that other modifications, variations and changes will be suggested to those skilled in the art in view of the teachings set forth herein. It is therefore to be understood that all such variations, modifications and changes are believed to fall within the scope of the present invention as described by the appended claims.

I claim:

1. A method for reducing cholesterol levels in human beings requiring such treatment comprising orally administering to said human being a therapeutically effective amount of a dopamine agonist selected from the group consisting of bromocriptine, lergotrile and pergolide, and an ascorbate.

2. The method according to claim 1 wherein said ascorbate is present as a metallic salt and the dopamine agonist is bromocriptine.

3. The method according to claim 2 wherein the metallic salt is sodium ascorbate.

4. The method according to claim 1 wherein the dopamine agonist is lergotrile.

5. The method according to claim 1 wherein the dopamine agonist is pergolide.

6. A method according to claim 1 wherein the dopamine agonist is administered in an amount ranging from 0.4 to 10.0 milligrams daily.

7. The method according to claim 6 wherein the ascorbate is administered in an amount ranging from 0.25 grams to 20 grams daily.

8. The method according to claim 1 additionally comprising coadministering 0.1 to 800 milligrams of a gonadal hormone on a daily basis.

9. The method according to claim 7 additionally comprising coadministering 0.1 to 800 milligrams of gonadal hormone on a daily basis.

* * * * *